US011672993B2

(12) United States Patent
Doerr et al.

(10) Patent No.: US 11,672,993 B2
(45) Date of Patent: Jun. 13, 2023

(54) IMPLANT

(71) Applicant: BIOTRONIK SE & Co. KG, Berlin (DE)

(72) Inventors: Thomas Doerr, Berlin (DE); Ulrich Feese, Berlin (DE); Rolf Klenner, Michendorf (DE); Torsten Oertmann, Blankenfelde (DE)

(73) Assignee: BIOTRONIK SE & Co. KG, Berlin (DE)

( * ) Notice: Subject to any disclaimer, the term of this patent is extended or adjusted under 35 U.S.C. 154(b) by 79 days.

(21) Appl. No.: 17/264,022

(22) PCT Filed: Jul. 22, 2019

(86) PCT No.: PCT/EP2019/069616
§ 371 (c)(1),
(2) Date: Jan. 28, 2021

(87) PCT Pub. No.: WO2020/025366
PCT Pub. Date: Feb. 6, 2020

(65) Prior Publication Data
US 2021/0316147 A1    Oct. 14, 2021

(30) Foreign Application Priority Data

Aug. 2, 2018   (EP) .................................... 18187090

(51) Int. Cl.
*A61N 1/375*   (2006.01)
*A61N 1/378*   (2006.01)
*A61N 1/39*    (2006.01)

(52) U.S. Cl.
CPC .......... *A61N 1/3754* (2013.01); *A61N 1/378* (2013.01); *A61N 1/37512* (2017.08); *A61N 1/3956* (2013.01)

(58) Field of Classification Search
CPC .. A61N 1/3754; A61N 1/378; A61N 1/37512; A61N 1/3956; A61N 1/3752; A61N 1/3758; A61N 1/375
See application file for complete search history.

(56) References Cited

U.S. PATENT DOCUMENTS

| 7,647,110 | B2 | 1/2010 | Hoernfeldt et al. |
| 9,713,717 | B2 | 7/2017 | Aghassian |
| 9,737,721 | B2 | 8/2017 | Bunyan et al. |
| 9,992,866 | B2 * | 6/2018 | Sporon-Fiedler .... H05K 3/0067 |
| 10,029,107 | B1 * | 7/2018 | Webb ................... A61N 1/3756 |
| 2004/0015199 | A1 * | 1/2004 | Thompson .......... A61N 1/3758 977/932 |

(Continued)

FOREIGN PATENT DOCUMENTS

EP    2493557 B1    5/2017

OTHER PUBLICATIONS

International Search Report (PCT/ISA/210) and translation and Written Opinion (PCT/ISA/237) dated Dec. 19, 2019, by the European Patent Office as the International Searching Authority for International Application No. PCT/EP2019/069616.

*Primary Examiner* — Catherine M Voorhees
(74) *Attorney, Agent, or Firm* — Buchanan Ingersoll & Rooney PC

(57) ABSTRACT

The disclosure relates to an implant comprising an electronics module and an energy store, wherein the volume of the electronics module is less than 25% of the volume of the energy store.

15 Claims, 15 Drawing Sheets

(56) References Cited

U.S. PATENT DOCUMENTS

| | | | |
|---|---|---|---|
| 2012/0319288 A1* | 12/2012 | Birge | H01L 23/49805 257/773 |
| 2013/0338750 A1* | 12/2013 | Eck | A61N 1/362 439/271 |
| 2015/0066112 A1 | 3/2015 | Parramon et al. | |
| 2016/0220827 A1* | 8/2016 | Bunyan | A61N 1/3754 |
| 2018/0005720 A1* | 1/2018 | Cabauy | G21H 1/06 |
| 2018/0054034 A1 | 2/2018 | Seeley et al. | |

* cited by examiner

IMPLANT

CROSS-REFERENCE TO RELATED APPLICATIONS

This application is the United States national phase under 35 U.S.C. § 371 of PCT International Patent Application No. PCT/EP2019/069616, filed on Jul. 22, 2019, which claims the benefit of European Patent Application No. 18187090.8, filed on Aug. 2, 2018, the disclosures of which are hereby incorporated by reference herein in their entireties.

TECHNICAL FIELD

The present disclosure relates to an implant.

BACKGROUND

An implant, such as a pacemaker or a defibrillator, contains, among other things, an electronics module with chips, a battery for power supply, and a feedthrough to a header, to which one or more electrodes may be connected. Currently known contact-establishing means between the electronics module, the battery, and the feedthrough are usually realised with soldered-on or welded-on contact-establishing strips. In alternative embodiments, bent battery pins are connected in plug-in contact-establishing means.

FIG. 1 shows an implant as known from the prior art. The implant comprises a housing 50, in which a battery 51 and an electronics module 52 are arranged. An electrode connection device (header) 53 is arranged on the housing 50. A first electrical contact 54 is formed between the electronics module 52 and the battery 51. A second electrical contact 56 is formed between the electronics module 52 and a feedthrough 55. The feedthrough 55 leads out of the housing 50 and provides an electrical connection between the electronics module 52 and the electrode connection device 53. The elements of the implant (electrode connection device 53, feedthrough 55, battery 51, and electronics module 52) are lined up flat next to each other. This results in each electrical connection between the elements (in particular the first electrical contact 54 and the second electrical contact 56) passing through an angle of 90°, thus requiring complex and costly construction processes. The production of the implant shown in FIG. 1 requires complex manufacturing technology and is difficult to automate.

U.S. Pat. No. 9,737,721 discloses an implant for stimulating the spinal cord. The implant comprises a housing, in which a battery and an electronics module are arranged. A support frame arranged on the battery accommodates the electronics module and a communication coil. The electronics module is arranged here perpendicular to the battery.

U.S. Pat. No. 7,647,110 describes a modular implant. Different connector modules, electronics modules, and battery modules may be combined to realise different functions.

European Patent No. 2 493 557 discloses a modular header for an implant. The header is constructed from a number of modules that are connected to each other. The length of the header may be adjusted by the number of modules.

United States Publication No. 2018/0054034 discloses a modular connector of which the length may be adjusted by means of the number of modules used.

U.S. Pat. No. 9,713,717 discloses an implant having an electronics module which is formed on a substrate. Some components of the electronics module, such as filter capacitors or blocking capacitors, are embedded in the substrate.

The present disclosure is directed toward overcoming one or more of the above-mentioned problems, though not necessarily limited to embodiments that do.

SUMMARY

An object is to specify improved technologies for implants. In particular, the production of an active medical implant is to be simplified.

An implant according to claim 1 is disclosed. Further embodiments are the subject of dependent claims.

According to one aspect, an implant having a housing is provided. An energy store and an electronics module are arranged in the housing. A feedthrough to an electrode connection device is formed on the housing. A first contact forms an electrical connection between the energy store and the electronics module. A second contact forms an electrical connection between the electronics module and the feedthrough. The first contact and the second contact are oriented in the same contact direction.

The implant may be an active medical implant, for example an implantable pacemaker or an implantable cardioverter-defibrillator (ICD).

The electrode connection device may also be referred to as a connection head or a header. The electrode connection device may be designed to receive one or more electrode connections.

The electronics module may have components that ensure the operation of the implant, for example a processor and a memory.

The energy store may comprise a primary cell, a secondary cell, a capacitor or any combination of the aforementioned elements. The energy store may be designed to supply the components of the electronics module with electrical energy. Furthermore, the energy store may be designed to provide electrical energy for defibrillation (shock). The energy store may be electrically insulated from the housing, for example by means of a cover made of an electrically insulating material (for example a thermoplastic such as PEEK (polyether ether ketone)), a firmly adhering plastics material coating made of an electrically insulating material, a one-part or multi-part insulating film, a coating made of an electrically insulating material (for example plastic), or by means of gluing an insulating film to the energy store. The feedthrough may provide an electrical connection between the electrode connection device and the electronics module. The feedthrough may be multi-pole, for example three-pole, four-pole or five-pole.

The housing may comprise a biocompatible material or be made of a biocompatible material (for example titanium).

An equal contact direction is given if a preferred direction of the first contact coincides with a preferred direction of the second contact, i.e. the contacts point in the same direction. The preferred direction of the contacts may result from the geometry of the contacts. In the case of a pin contact, the preferred direction is a longitudinal extension of the pin. In the case of planar contact, the preferred direction is the normal of the surface.

It may be provided that the energy store, the electronics module, and the feedthrough are arranged one above the other in a stacking direction, wherein the stacking direction corresponds to the contact direction. The energy store, the electronics module and the feedthrough are assembled in a single assembly direction. Stacking the elements on top of each other simplifies the assembly of the implant and facilitates automation of the production process. Furthermore, the electrode connection device may be arranged on the housing in the stacking direction.

The first contact may be formed between a first planar contact element arranged on the energy store and a second planar contact element arranged on the electronics module, wherein the contact direction is the normal of a contact area between the first planar contact element and the second planar contact element. The first planar contact element and the second planar contact element may be of the same size. The first planar contact element and the second planar contact element may have the same shape, for example square, rectangular, round or oval. The first planar contact element and the second planar contact element may be symmetrical.

The second contact may be formed between a third planar contact element arranged on the electronics module and a fourth planar contact element arranged on the feedthrough, wherein the contact direction is the normal of a contact area between the third planar contact element and the fourth planar contact element. The third planar contact element and the fourth planar contact element may be of the same size. The first planar contact element and the second planar contact element may have the same shape, for example square, rectangular, round or oval. The third planar contact element and the fourth planar contact element may be symmetrical.

In one embodiment, it may be provided that the first contact is formed between a first pin element and a first pin receptacle, wherein a longitudinal extension of the first pin element determines the contact direction. The first pin element may be arranged on the energy store. In this case, the first pin receptacle is arranged on the electronics module. In another variant, the first pin element may be arranged on the electronics module and the first pin receptacle is arranged on the energy store. The first pin element may comprise a plurality of pins oriented parallel to each other. It may be provided that the first pin element is formed as a pair of pins arranged, for example, on the energy store (for example as an anode and cathode of the energy store). In this case, the first pin receptacle is formed as a pair of pin receptacles that may be arranged, for example, on the electronics module.

Furthermore, it may be provided that the second contact is formed between a second pin element and a second pin receptacle, wherein a longitudinal extension of the second pin element determines the contact direction. The second pin element may be arranged on the feedthrough, wherein the second pin receptacle is arranged on the electronics module. Alternatively, the second pin element may be arranged on the electronics module and the second pin receptacle is arranged on the feedthrough. The second pin element may comprise a plurality of pins oriented parallel to each other. For example, the plurality of pins may be arranged on the feedthrough (multi-pole feedthrough). In this case, the second pin receptacle comprises a plurality of pin receptacles arranged, for example, on the electronics module.

The first pin element and the second pin element may be arranged parallel to each other.

The first contact and/or the second contact may be designed as a plug-in contact, clamping contact or welding contact.

The electronics module may be arranged on a front side of the energy store. The front side is the side of the energy store facing the electrode connection device. The electronics module is therefore arranged between the electrode connection device and the energy store.

The electronics module may be arranged parallel or perpendicular to the front side of the energy store. The electronics module may have a planar substrate on which components are arranged. In the case of the planar substrate, the height of the substrate is much smaller than the width and length of the substrate. The substrate may be in the form of a printed circuit board. The planar substrate may be arranged parallel or perpendicular to the front side of the energy store. In particular, a parallel arrangement of the electronics module/substrate enables space-saving assembly. In this case, the electronics module is located on the front side of the energy store.

It may be provided that the electronics module is arranged in a support frame. The support frame may be arranged in the housing in such a way that the energy store is fixed by the support frame. The support frame may be arranged with a press fit on the energy store so that the energy store is pressed against the housing by the support frame and is thereby fixed. Alternatively or additionally, it may be provided that the support frame is designed and arranged in the housing in such a way that the support frame reduces or prevents a relative movement between the energy store and the electronics module. In particular, a relative movement that leads to the loss of the electrical connection between the electronics module and the energy store is to be prevented. The support frame may comprise a plastics material or be made entirely of a plastics material. Suitable plastics materials are, for example, polybutylene terephthalate (PBT), polycarbonate (PC) or similar plastics materials.

The housing may be formed in two parts and have a first housing shell and a second housing shell. It may be provided that the energy store is fixed between the first housing shell and the second housing shell. The first housing shell and the second housing shell may be symmetrical (for example mirror symmetrical) or identical. The two-part housing may have integrated welding protection (for example a beading).

In one embodiment, the housing may be formed in one part. The one-part housing may be produced by direct molding from a base material, for example by deep drawing.

The housing may have an opening, wherein it is possible to introduce the energy store and the electronics module into the housing through the opening. The opening may be formed on a front side (the side facing the electrode connection device) of the housing. If the housing is in two parts, the first housing shell and the second housing shell may be connected to each other (for example welded) so that the opening is formed on the front side. The opening may be open in the contact direction. In this case, all elements of the implant (the energy store, the electronics module, the feedthrough, the electrode connection device, and the housing) may be assembled in a single stacking direction.

The energy store may be fastened to the enclosure. For example, a self-adhesive pad may be attached to the first housing shell and/or to the second housing shell, to which pad(s) the energy store adheres when the housing shells are connected to form the housing. It may also be provided that the energy store is glued by means of an adhesive to the first housing shell and/or to the second housing shell. The fixing may also be realised by a clamping action between the first housing shell and the second housing shell. It may also be provided that the housing is welded to the energy store.

A clamping part may be arranged in the housing, wherein the clamping part is designed to fix the energy store relative to the housing. The clamping part may be arranged in a lower portion of the housing, which is opposite the front side of the housing. The clamping part may be designed to press the energy store against the support frame for fixing. The clamping part may be designed as a spring, as a welding protection band or as a solid, space-filling plastics material part.

The feedthrough may be attached to the electronics module as an SMD (surface-mounted device) component. An SMD component is soldered directly to a printed circuit board (for example the substrate of the electronics module) by means of one or more solderable connection areas. In other words: The feedthrough is assembled on the electronics module using SMT (surface-mounting technology).

The feedthrough may have a second substrate. The second substrate of the feedthrough, the electronics module (or the substrate of the electronics module) and the front side of the energy store may be arranged parallel to each other.

According to a further aspect, a method for assembling an implant is disclosed. The method comprises the steps of: providing an energy store, providing an electronics module, providing a feedthrough, arranging the electronics module on the energy store, and arranging the feedthrough on the electronics module. Here, the feedthrough, the electronics module, and the energy store are arranged on top of each other along a common assembly direction. In particular, the electronics module may be arranged on a front side of the energy store.

The order of arrangement is not important. The electronics module may be arranged on the energy store first and then the feedthrough on the electronics module. However, the feedthrough may also be arranged on the electronics module first and then the electronics module with the feedthrough is arranged on the energy store.

When arranging the electronics module on the energy store, an electrical connection between the energy store and the electronics module may be formed with a first contact. When arranging the feedthrough on the electronics module, an electrical connection between the electronics module and the feedthrough may be formed with a second contact. The first contact and the second contact may be oriented in the same contact direction.

The method may further comprise the following steps: arranging the energy store with the electronics module and the feedthrough in a housing and closing the housing.

The method may further comprise the following steps: arranging an electrode connection device on the housing and connecting the electrode connection device to the feedthrough.

According to a further aspect, an implant comprising an electronics module and an energy store is provided, wherein the volume of the electronics module is less than 25% of the volume of the energy store. Preferably, the volume of the electronics module is less than 20% of the volume of the energy store. More preferably, the volume of the electronics module is less than 16% of the volume of the energy store. In one embodiment, the volume of the energy store is 3.06 cm$^3$ and the volume of the electronics module is 0.46 cm$^3$.

The elements of the implant are three-dimensional objects, each with a length, a width, and a height. The dimensions of the objects are always determined in the same direction. The length of the electronics module is determined in the same direction as the length of the electrode connection device and the length of the battery. The width of the electronics module is determined in the same direction as the width of the electrode connection device and the width of the battery. The height of the electronics module is determined in the same direction as the height of the electrode connection device and the height of the battery. In the lower left corner of FIG. 2 a coordinate system is drawn for illustration. The x-direction corresponds to the length, the y-direction indicates the width, and the z-direction corresponds to the height.

The volume of the energy store is the actual volume of the element.

The volume of the electronics module is considered to be the volume of an envelope around the electronics module, wherein the base of the envelope is equal to the area of the electronics module and the height of the envelope is equal to the height of the highest component on the electronics module. If the electronics module has a rectangular base, the volume is thus given by a cuboid, wherein the base of the cuboid is equal to the base of the electronics module (product of the length and the width). The height of the cuboid corresponds to the height of the highest component on the electronics module. If the electronics module is embodied as a planar substrate, components may be arranged on one side of the substrate. In this case, the above definition for the volume applies. It may also be provided that components are arranged on both sides of the substrate. In this case, the height of the electronics module corresponds to the sum of the heights of the highest component on each side of the substrate.

The ratio of the length of the electronics module to the width of the electronics module may be 4:1 or more, preferably 5:1 or more, more preferably 6:1 or more. In this embodiment, the electronics module has a narrow design, which may facilitate arrangement of the electronics module on the front side of the energy store. In one embodiment, the electronics module has a length of more than 30 mm and a width of less than 5.2 mm.

It may be provided that the width of the electronics module is smaller than or equal to the width of the energy store.

The length of the electronics module may be less than or equal to the length of the energy store.

As already explained above, the implant may comprise an electrode connection device, wherein the length of the electronics module is less than or equal to the length of the electrode connection device, and/or wherein the width of the electronics module is less than or equal to the width of the electrode connection device. It may also be provided that the length of the energy store is less than or equal to the length of the electrode connection device and/or that the width of the energy store is less than or equal to the width of the electrode connection device.

The electronics module may have a substrate on which a plurality of components are arranged, wherein the area of the substrate is less than or equal to the area of the front side of the energy store.

It may be provided that some of the plurality of components have a minimum structure size of $F \leq 90$ nm. Alternatively or additionally, it may be provided that some (or other) of the plurality of components have a minimum structure size of $F \leq 65$ nm, preferably $F \leq 55$ nm. It may be provided that all of the components of the electronics module are manufactured with a uniform structure size, for example $F \leq 90$ nm, $F \leq 65$ nm or $F \leq 55$ nm. It may also be provided that the components of the electronics module are manufactured with different structure sizes mentioned here.

At least one of the plurality of components may be arranged on a first side of the substrate and at least one other of the plurality of components may be arranged on a second side of the substrate. The substrate may therefore be populated on one side or on two sides.

In one embodiment, it may be provided that the at least one component on the first side of the substrate and/or the at least one other component on the second side of the substrate are encapsulated with a potting agent.

It may also be provided that some of the plurality of components are arranged as SMD elements on the substrate. For example, the components may be arranged in one or more Ball Grid Array (BGA) and/or Multi Chip Module (MCM) housings and/or as bare integrated circuits (chips). If the substrate is populated on one side, the following arrangements of the components are possible:
- all components are arranged in a ball grid array package,
- all components are arranged in an MCM package,
- all components are arranged as chips,
- all components are arranged as SMD elements, and
- one or some or none of the components are arranged in one or more BGA housings, one or some or none of the other components are arranged in one or more MCM housings, one or some or none of the other components are arranged as chips, and one or some or none of the other components are arranged as SMD elements.

In the case of a two-sided population of the substrate, the above-mentioned arrangements may be realised for both sides of the substrate.

It may be provided that some of the plurality of components are arranged side by side or on top of each other on one side of the substrate, wherein the chips/components each are bonded to the substrate, and wherein the components are encapsulated with a potting agent. The connection of the chips/components to the substrate may be in the form of wire bonds, flip chip bumps or flip chip solder ball connections. The potting agent may partially cover the substrate. In one embodiment, the potting agent may extend along an edge of the substrate. Preferably, the potting agent completely covers the side of the substrate on which the components are arranged.

On a panel serving as a substrate, the components may be arranged in a grid such that each grid cell has all the units/chips required for an electronics module. Each chip/component is bonded to the substrate to make the electrical connections. The panel is then encapsulated with a potting agent (overmolding). After the panel is covered with the potting agent, the individual electronics modules are sawn out of the panel. Advantageously, the length of the potting area on the panel is an integer multiple of the length of the electronics module and/or the width of the potting region on the panel is an integer multiple of the width of the electronics module. This makes optimal use of the potting area of the panel. On another side of the panel/substrate, further components may be arranged, for example as SMD elements, in chips and/or in ball grid array packages.

Holes for a connection contact for the energy store and/or for a further connection contact for a feedthrough may be formed in the potting agent.

The electronics module may be formed as a multi-chip module. A multi-chip module (MCM) consists of a plurality of individual microchips that are accommodated in planar fashion (side by side) or on top of each other in a common package and look from the outside like one chip and also function and are used like one chip.

The feedthrough to the electrode connection device may be formed as a:
- integral component of the electronics module,
- SMD component on the electronics module, or
- plug-in connection on the electronics module.

According to another aspect, an implant comprising an electronics module and an electronic component is provided, wherein an electrical connection between the electronics module and the electronic component is formed by a straight plug-in connection.

The implant may have a further electronic component, wherein an electrical connection between the electronics module and the further electronic component is formed by a further straight plug-in connection, and wherein the straight plug-in connection and the further straight plug-in connection are oriented in the same direction. The features disclosed here for the straight plug-in connection apply analogously to the further straight plug-in connection. Likewise, the explanations for the electronic component apply analogously to the further electronic component.

The electrical connection may be designed wholly or partially as a plug-in contact in such a way that a contact pin (or plurality of contact pins) of the electronic component may be plugged directly into or through a male connector receptacle of the electronics module. The straight plug-in connection is free of an adapter (for example a wiring strip); furthermore, bending of the pin is not necessary.

The electronic component or the further electronic component may be a feedthrough or an energy store. A plurality of electronic components may be provided, wherein an electrical connection to the electronics module is formed with a straight plug-in connection for each electronic component. The electronics module and the electronic component(s) may be arranged in a package.

In one embodiment, a further electronics module may be arranged on the electronics module. The further electronics module may be connected to the electronics module by means of a straight plug-in connection. A stack of a plurality of electronics modules may be formed, wherein the plurality of electronics modules each are connected to one another by a straight plug-in connection.

The electronic component may comprise a straight pin element, wherein the electronics module comprises a pin receptacle, and wherein the pin element is arranged in the pin receptacle in order to form the electrical connection.

Alternatively, the electronic module may comprise a straight pin element, wherein the electronic component comprises a pin receptacle, and wherein the pin element is arranged in the pin receptacle in order to form the electrical connection.

As explained above, the straight pin element may comprise a plurality of pins. The plurality of pins may be arranged parallel to each other. In this case, a plurality of pin receptacles are provided, wherein each of the plurality of pins is associated with a separate one of the plurality of pin receptacles.

The pin receptacle may be ring-shaped. The pin receptacle may be embodied as a disc. The pin receptacle may be soldered to the electronics module or to the electronic component. The pin element may be welded in the pin receptacle.

The pin receptacle may be fastened to the electronics module using one of the following fastening methods: soldering, gluing, embedding, clamping, and crimping. Crimping is understood to mean a joining process in which two components are joined together by plastic deformation, for example by flanging, squeezing, rippling or folding. In embedding, part of the pin receptacle is enclosed by the material of the electronics module.

The pin receptacle may be fastened to the electronic component using one of the following fastening methods: soldering, gluing, embedding, clamping, and crimping.

It may be provided that the pin element has a spring element.

The electronic component may be an energy store, a feedthrough, or a capacitor. The electronic component may furthermore be embodied as a high-voltage capacitor or a capacitor stack. In one embodiment, the electronic component is an energy store and the further electronic component is a feedthrough.

The plug-in connection may be formed as a detachable connection, for example as a plug-in connection.

The plug-in connection may be formed as a non-detachable connection, for example as a welded connection or soldered connection.

The electrical connection may be formed with a connection selected from the following connection types: spring contact, insulation displacement contact, solder contact, weld contact, press fit, and adhesive. An electrically conductive adhesive may be used for an adhesive connection.

The plug-in connection may be designed to compensate for a relative movement between the electronic component and the electronics module without interrupting the electrical connection. For example, the pin element may be sufficiently long and flexible to compensate for a relative movement of the electronic component with respect to the electronics module. Alternatively or additionally, the male connector receptacle may be sufficiently flexible and/or mounted in a sufficiently flexible manner to compensate for a relative movement of the electronic component with respect to the electronics module. For example, the pin element may have a length that is greater than a height of the pin receptacle. In this case, the pin element projects beyond the pin receptacle in the inserted state, so that a movement along the direction of the pin element may be compensated for within a certain range.

According to yet another aspect, there is provided a method for producing an electrical connection between an electronics module and an electronic component of an implant, wherein the electronic component and the electronics module are moved towards each other with a relative movement, and the electrical connection is formed with a straight plug-in connection between the electronic component and the electronics module. The relative movement may be a straight relative movement. This facilitates the implementation of an automated process for assembling the implant.

The plug-in connection may be designed as a redundant connection to increase reliability.

According to yet another aspect, an implant comprising an electrode connection device and a housing is disclosed, wherein a cover for closing the housing is formed on the electrode connection device.

The cover may be welded to the housing. It may be provided that a flange is formed on the cover. The flange may run partially or completely along a circumference of the cover.

A welding protection device may be formed on the cover, for example in the form of a partial or complete circumferential beading.

The cover may alternatively be fastened to the housing by means of a plug-in connection, a spring connection or a clamp connection.

The cover may be formed from a biocompatible material, for example titanium.

The cover and the housing may be formed from the same material (for example titanium).

A feedthrough may be formed in the cover, wherein the feedthrough forms an electrical connection between the electrode connection device and an electronics module arranged in the housing.

The feedthrough may be electrically connected to the electronics module by a plug-in connection or by a spring contact.

The electrode connection device may comprise a pre-assembled assembly. The assembly may comprise the following components: a continuous receiving means for a male connector; a first connection element arranged in a front portion of the receiving means, wherein the first connection element has at least two flat side faces; and a second connection element arranged in a rear region of the receiving means, wherein the second connection element has at least two flat side faces.

According to a further aspect, an assembly for an electrode connection device of an implant is provided. The assembly comprises a continuous receiving means for a male connector. Further provided is a first connection element arranged in a front region of the receiving means, wherein the first connection element has at least two flat side faces. Lastly, a second connection element is provided and is arranged in a rear region of the receiving means, wherein the second connection element has at least two flat side faces.

Further provided is an electrode connection device for an implant comprising an assembly disclosed herein.

The disclosure further comprises an implant having an electrode connection device and an assembly.

The flat side faces enable an at least partially angular shape and allow easy gripping of the assembly (manually or automatically). This may enable automation of the production process.

The assembly may be surrounded by a plastics material at least in some sections. For example, the assembly may be overmolded by the plastics material in some sections. The plastics material may be a thermoplastic, for example polysulfone. A biocompatible casting resin may also be used. The plastics material may provide additional stability to the assembly. Hereby, it is possible to produce the assembly as a prefabricated component, which is subsequently processed into an electrode connection device of an implant.

A connection region of the first connection element may be free of plastics material. Alternatively or additionally, a connection region of the second connection element may be free of plastics material.

A first guide for a first conductor for connection to the connection region of the first connection element may be formed in the plastics material and/or a second guide for a second conductor for connection to the connection region of the second connection element may be formed in the plastics material.

The first guide may be formed adjacently to the connection region of the first connection element and/or the second guide may be formed adjacently to the connection region of the second connection element.

A first conductor (second conductor) may be connected to the connection region of the first connection element (the second connection element) in order to enable a connection of a male connector inserted into the receiving means to an implant. The connection region of the first connection element and/or the connection region of the second connection element may be embodied as planar elements. The connection region of the first connection element and/or the connection region of the second connection element may be circular and have a diameter of 1 to 5 mm, for example. This provides a large welding area for fastening the first conductor or the second conductor. In one embodiment, both the first guide and the second guide are formed adjacently to their respective connection regions. The guides allow the conductors to be connected to their respective connection regions without causing a short circuit.

It may be provided that the first connection element and the second connection element are arranged offset to each other. In other words, the first connection element and the second connection element are on two different levels. The different arrangement makes it easier to connect the conductors to the connection elements without the conductors coming into contact with each other.

In one embodiment, the assembly may comprise an antenna, wherein the antenna has a U-shaped configuration in an intermediate region formed between the first connection element and the second connection element. The intermediate region may be narrower than the adjacent connection elements. Together with the U-shaped configuration of the antenna, a gripping recess for an automatic gripper is thus formed.

A positioning means may be formed at a rear end of the receiving means. The positioning means may be formed as an angled structure and may, for example, form a right angle to the receiving device. The positioning means may be formed from the plastics material and may be formed in one part with, for example, the plastics material coating of the assembly. The positioning means may be arranged on a housing of the implant when arranging the assembly in a receptacle to facilitate the orienting of the assembly. The positioning means may have a tapered end.

The assembly may have a further receiving means for a further male connector, wherein a third connection element is arranged in a front region of the further receiving means, and wherein a fourth connection element is arranged in a rear region of the further receiving means. For the further receiving means, the explanations disclosed here apply analogously to the receiving means. Furthermore, the explanations for the first connection element and the second connection element apply analogously to the third connection element and the fourth connection element.

According to a further aspect, a method for forming an electrode connection device on an implant is disclosed. The method comprises the steps of:
providing an assembly having:
  a continuous receiving means for a male connector,
  a first connection element arranged in a front region of the receiving means, wherein the first connection element has at least two flat side faces, and
  a second connection element arranged in a rear region of the receiving means, wherein the second connection element has at least two flat side faces,
arranging and fixing a spring element in the receiving means,
closing openings of the receiving means with potting aids,
fastening a first conductor to the first connection element,
fastening a second conductor to the second connection element,
arranging the assembly on a housing of the implant,
connecting the first conductor to a feedthrough formed on a housing,
connecting the second conductor to the feedthrough,
arranging the assembly with the housing in a mold,
filling the mold with a synthetic resin, and
after the resin has cured, removing the potting aids.

The method may also be used to form an electrode connection device on a cover of an implant.

The method may comprise the following further steps:
arranging and fastening an antenna to the assembly, and connecting the antenna to the feedthrough,
wherein the further steps are carried out before the assembly is arranged on the housing. Furthermore, it may be provided to remove any protruding resin after the curing, for example by means of grinding and/or polishing.

The mold may be a silicone mold.

The feedthrough may have one or more plug-in contacts (for example pins) for connecting the conductors and/or the antenna.

The synthetic resin may be an epoxy resin. Epoxy resins are synthetic resins that carry epoxy groups. They are curable resins (reactive resins) that may be reacted with a hardener and, if necessary, other additives to form a thermoset plastics material. Epoxy resins are polyethers with two terminal epoxy groups. The curing agents are reaction partners and together with the resin form a macromolecular plastics material.

The synthetic resin may adhere directly to the housing of the implant or to the cover of the implant, so that an additional adhesive is not required. In other words, the contact area between the cured resin and the housing/cover of the implant may be free of an adhesive.

The electrode connection device may be a header for an implantable cardiac pacemaker or an implantable cardioverter defibrillator (ICD). In this case, the electrode connection device is used to electrically connect one or more electrode leads to the implant.

An antenna, a charging coil, an X-ray marker, a communication coil and/or a colour marker may be arranged in the electrode connection device.

Another aspect relates to a method for producing an implant, comprising the following steps: providing a housing, providing an electrode connection device, wherein a cover is formed on the electrode connection device for closing the housing, arranging the cover on the housing, and connecting the cover to the housing. The connection between the cover and the housing may be formed as a material connection, for example by means of welding.

The aspects disclosed here concerning the implant and the assembly for the electrode connection device as well as the aspects concerning the methods may be combined with each other in any way to realise different embodiments of the implant or the methods. Furthermore, the explanations regarding the implant and the assembly apply analogously to the methods, and vice versa.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Exemplary embodiments are explained in more detail below with reference to the figures, in which.

DETAILED DESCRIPTION

Figure 1:
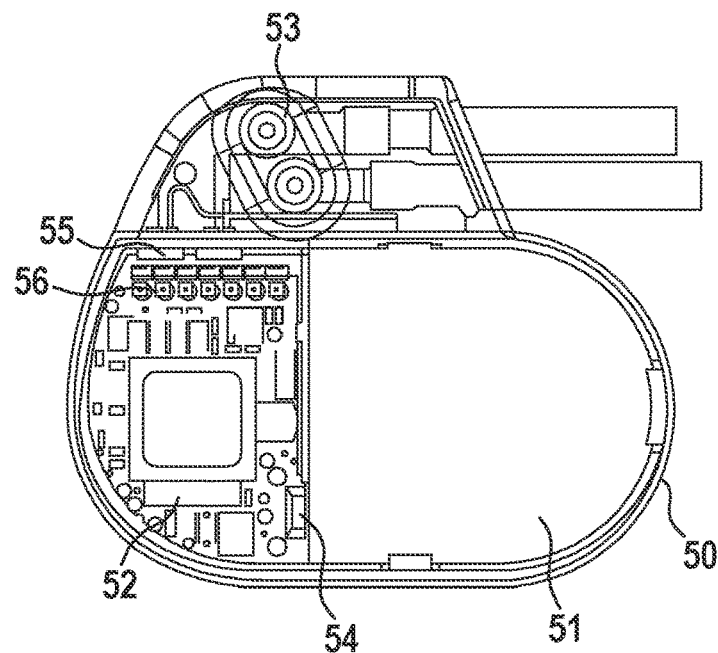
FIG. 1 shows a schematic representation of an implant according to the prior art.
Figure 2:
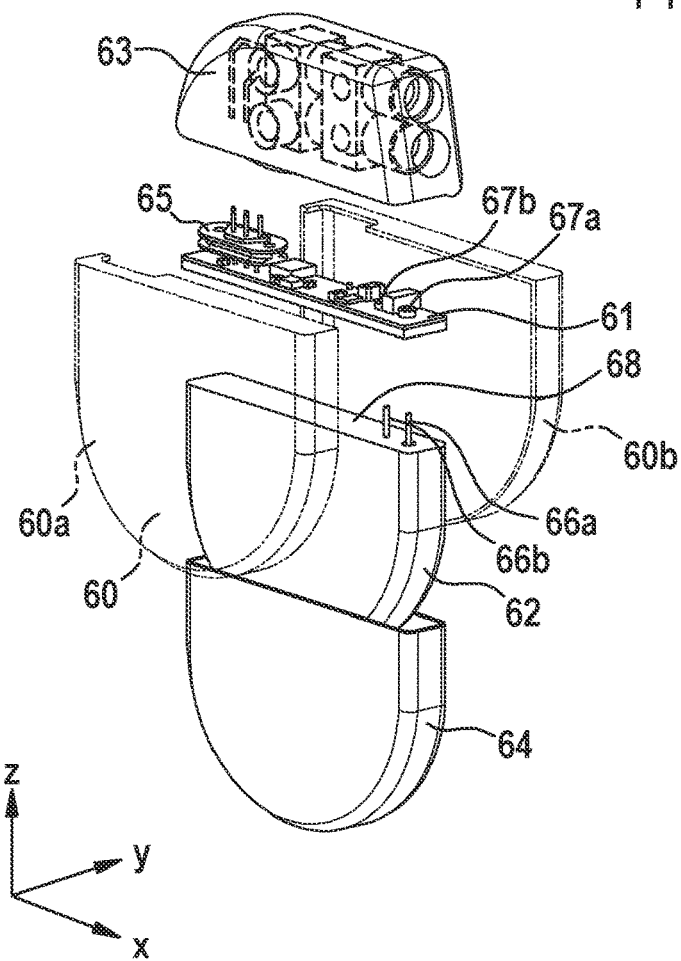
FIG. 2 shows an exploded view of an embodiment of an implant according to the present invention.

FIG. 2 shows an embodiment of an implant according to the present invention. The implant comprises a two-part housing 60 with a first housing shell 60a and a second housing shell 60b. An electronics module 61 and an energy store 62 (for example a battery) are arranged in the housing 60. The energy store 62 is electrically insulated from the housing 60 by means of an insulating cover 64. The electronics module 61 is arranged on a front side 68 of the energy store 62. A first pin element is arranged on the front side 68 of the energy store 62 and comprises two pins 66a, 66b oriented parallel to each other. Associated with the first pin element is a first pin receptacle which comprises two ring-shaped pin receptacles 67a, 67b and which is arranged on the electronics module 61. By means of the first pin element 66a, 66b and the first pin receptacle 67a, 67b, an electrical connection is formed between the energy store 62 and the electronics module 61. The electronics module 61 is connected to a feedthrough 65. Details of the connection are explained in greater depth below. An electrode connection device 63 is arranged on the housing 60 and is connected to the electronics module 61 by means of the feedthrough 65.

The feedthrough 65, the electronics module 61 and the energy store 62 are assembled along an axis (here along the z-direction). The direction of the axis is determined by the direction of the electrical connection between the feedthrough 65 and the electronics module 61 and the electrical connection between the electronics module 61 and the energy store 62.

In the embodiment shown, the electronics module 61 is arranged parallel to the front side 68 of the energy store 62. This type of arrangement uses the space in the housing very efficiently. The electronics module 61 may be plugged onto the front side 68 of the energy store 62 and/or glued to the front side 68.

Figure 3:
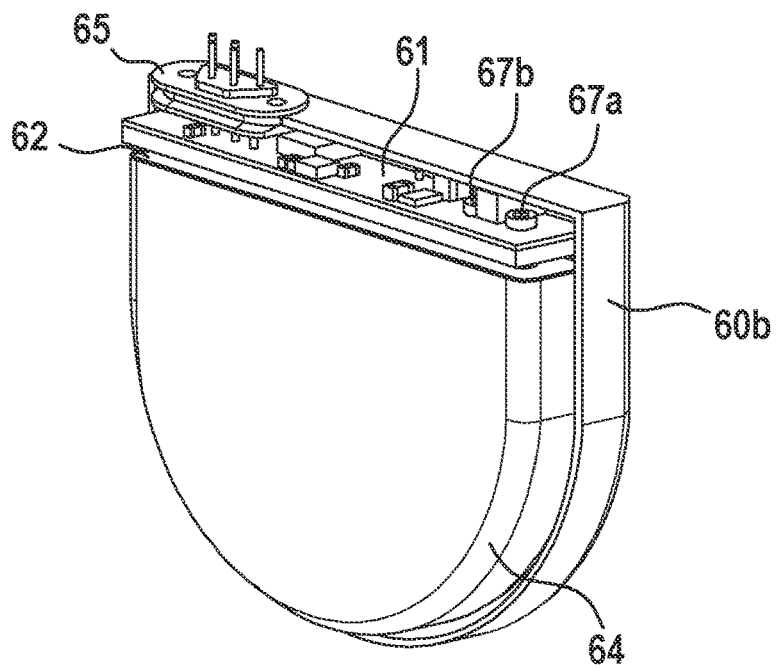
FIG. 3 shows a perspective view of a part of the implant according to FIG. 2.

In FIG. 3, the elements of the implant are partially assembled. The electronics module 61 is fitted on the energy store 62. Furthermore, the feedthrough 65 is connected to the electronics module 61. The energy store 62 (in the insulating cover 64) with the electronics module 61 is arranged in the second housing shell 60b. In the next step, the first housing shell 60a is arranged on the second housing shell 60b and the housing shells 60a, 60b are joined together, for example welded (not shown). Subsequently, the electrode connection device 63 is placed on the housing 60 and connected to the feedthrough 65 (not shown).

Figure 4:
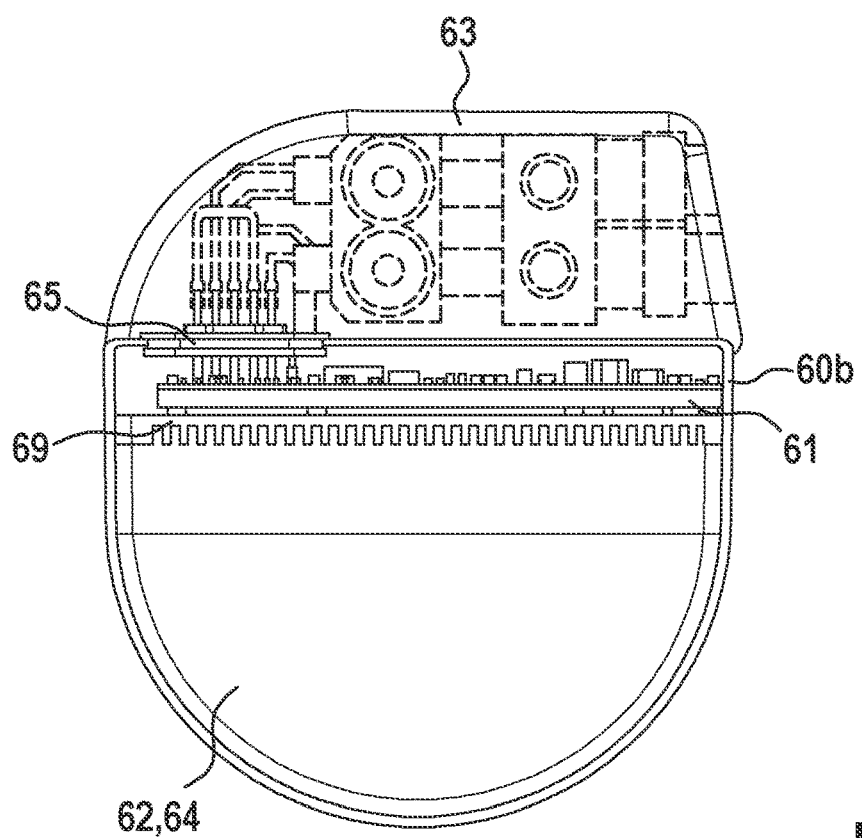
FIG. 4 shows a side view of an implant.

FIG. 4 shows a side view of an implant that corresponds substantially to the implant in FIG. 2. Like elements are therefore designated by like reference signs. In the embodiment according to FIG. 4, the electronics module 61 is arranged in a support frame 69. The support frame 69 is arranged on the front side of the energy store 62. The support frame 69 serves to centre the energy store 62 in the housing 60 and presses it against the housing base. This prevents the transmission of vibrations as well as compressive and tensile forces. The support frame 69 thus protects the components on the electronics module 61 as well as the electrical connection between the energy store 62 and the electronics module 61 from destruction and/or loss of electrical contact.

Figure 5:
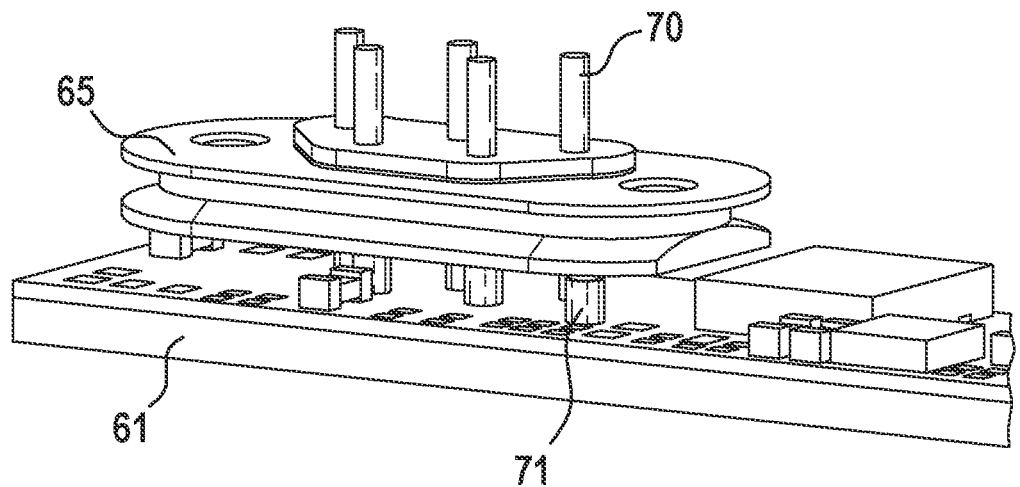
FIG. 5 shows a detail of the electronics module.
Figure 5:
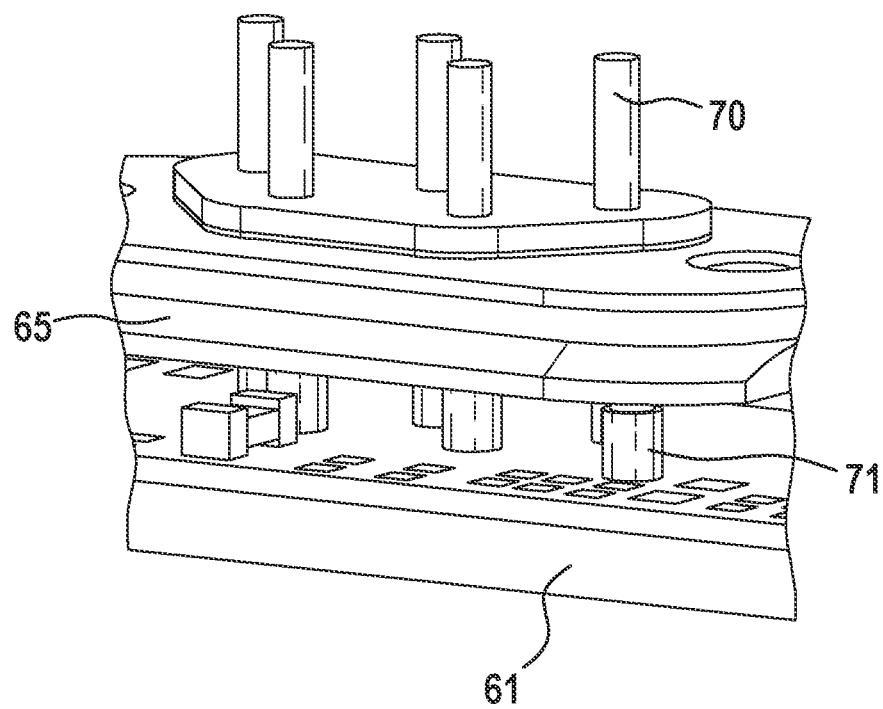

A detail of the electronics module 61 is shown in FIG. 5 (the lower part of FIG. 5 shows an enlarged detail of the upper part). The feedthrough 65 is formed as a multi-pole feedthrough with a plurality of pins 70. In the embodiment shown, five pins 70 are formed on the feedthrough 65, but a different number of pins is also possible. Each pin 70 is inserted into a pin receptacle 71 to form an electrical connection between the electronics module 61 and the electrode connection device 63 by means of the feedthrough 65.

Figure 6:
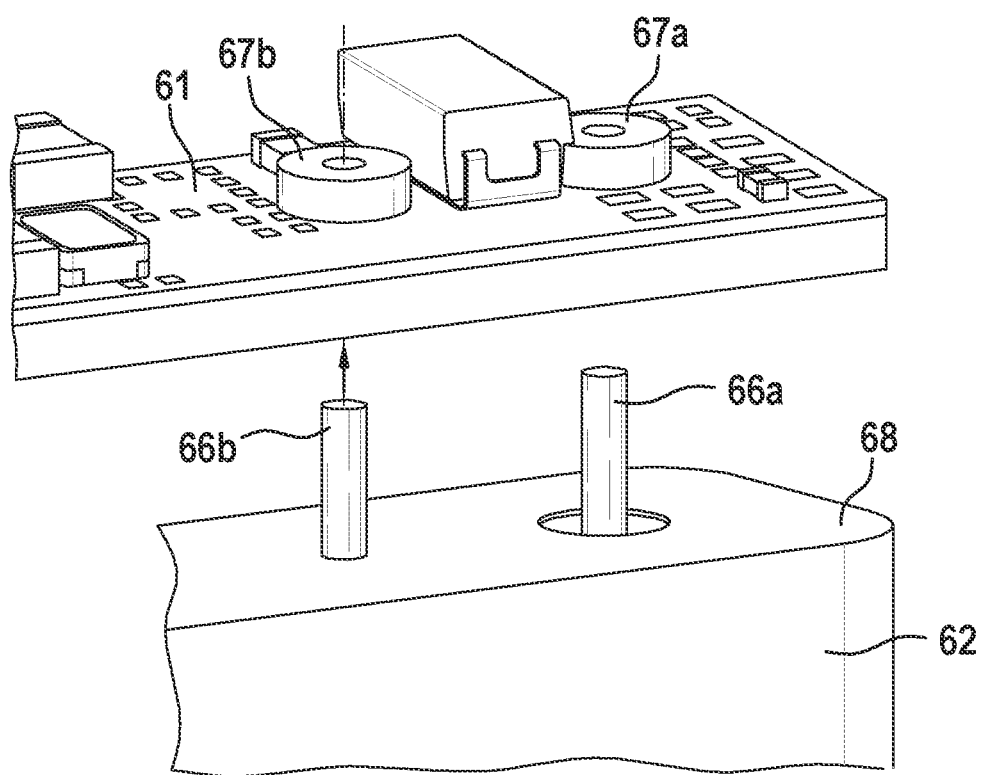
FIG. 6 shows a further detail of the electronics module.

Another detail of the electronics module together with a detail of the energy store 62 is shown in FIG. 6. The first pin element 66a, 66b (for example anode and cathode of the battery) is formed on the energy store. The first pin receptacle 67a, 67b is arranged on the electronics module 61. The electronics module 61 is electrically connected to the energy store 62 by means of a straight plug-in connection by inserting the first pin element 66a, 66b into the first pin receptacle 67a, 67b. The connection may be embodied as a redundant connection, for example in that the first pin receptacle 67a, 67b in each case comprises two pin receptacles arranged one above the other (two rings arranged one above the other) (not shown).

The electrical connection between the electronics module 61 and the energy store 62 may be realised with the following technologies:
as a cylinder with bore with laser welding (see FIG. 6),
as a spring contact in a plug-in connection, and
as an angle on the electronics module with resistance welding.

The pins 70 of the feedthrough 65 and the first pin element 66a, 66b point in the same direction (contact direction), which determines the assembly direction for the elements.

Figure 8:
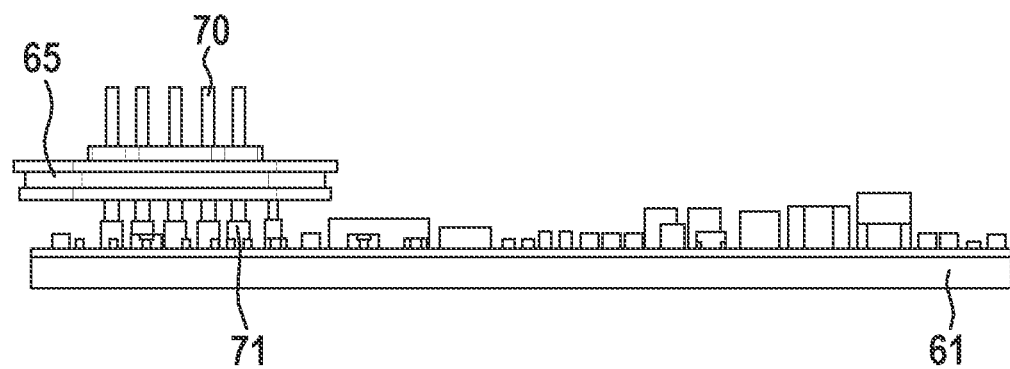
FIG. 8 shows a side view of the electronics module (upper image of FIG. 8), a view of the electronics module from below (middle image of FIG. 8) and a view of the electronics module from above (lower image of FIG. 8)
Figure 8:
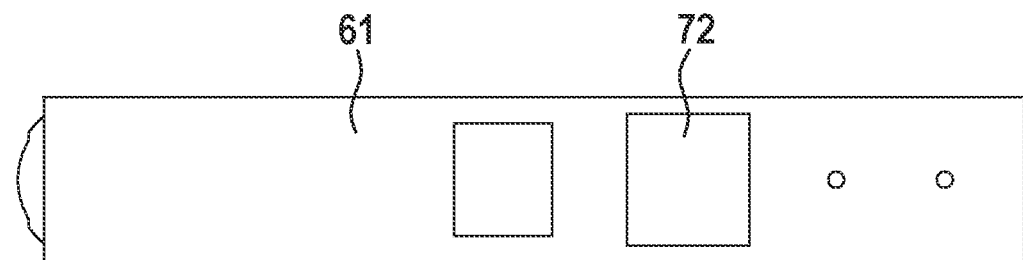
Figure 8:
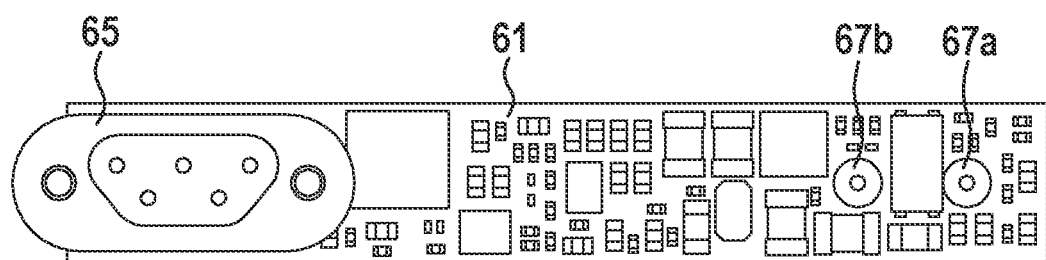
Figure 9:
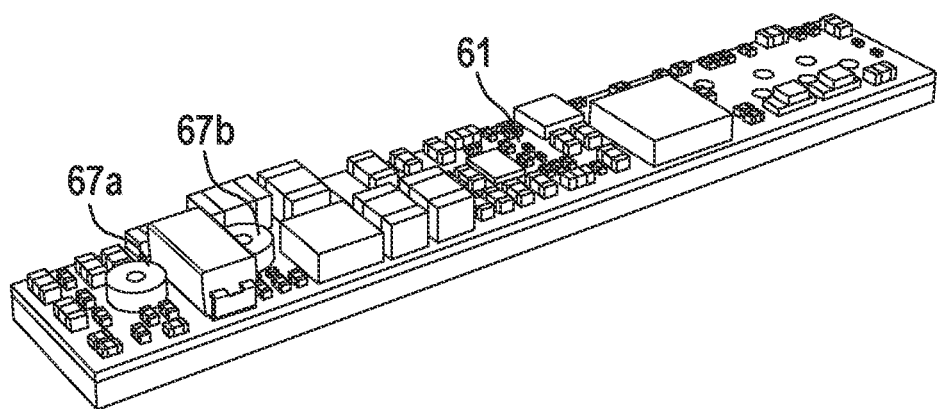
FIG. 9 shows a perspective view of the top side of the electronics module (upper image of FIG. 9) and a perspective view of the underside of the electronics module (lower image of FIG. 9)
Figure 9:
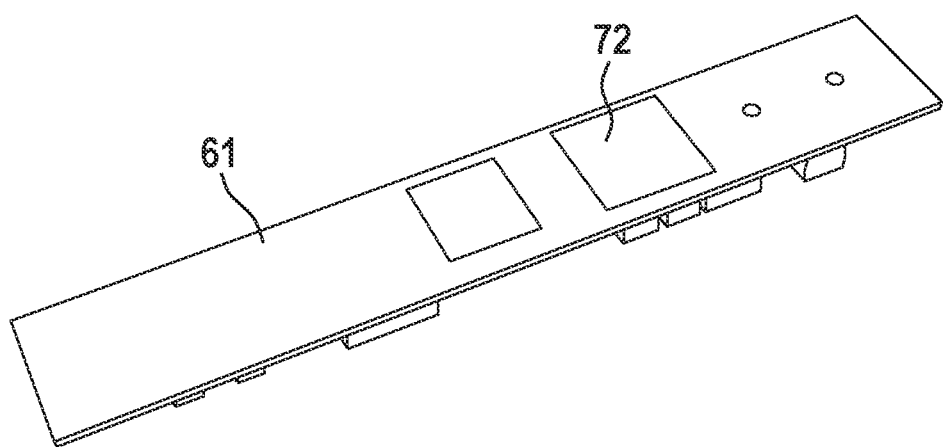

An SMD component 72 is arranged on a rear side of the electronics module (see FIGS. 8 and 9).

Figure 7:
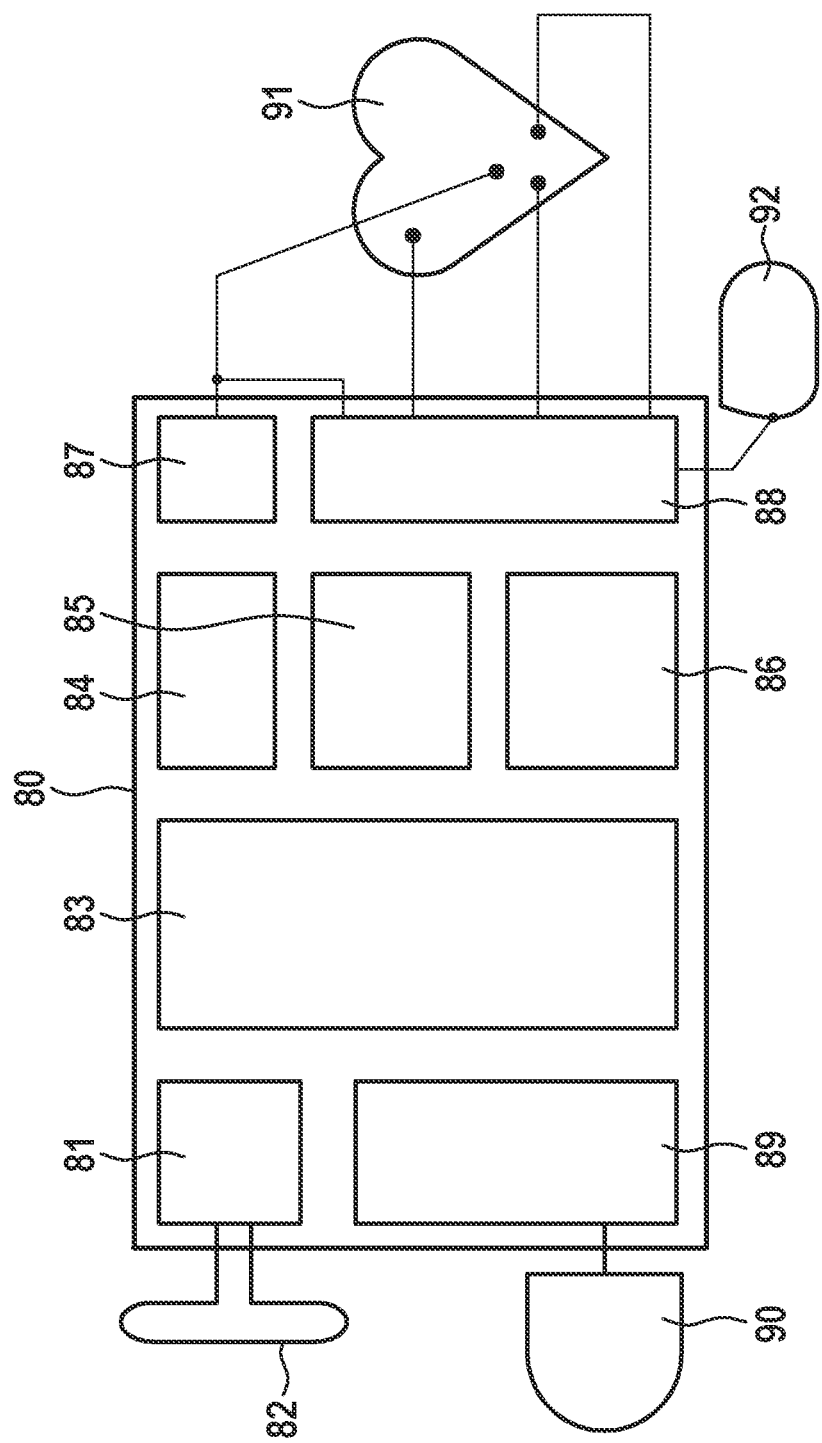
FIG. 7 shows a block diagram of the implant according to the present invention.

FIG. 7 shows a block diagram of the implant. The functions of the electronics module are surrounded by the frame 80 and are realised as units/chips on the electronics module and are explained in more detail below.

A radio transceiver 81 is coupled to an antenna 82. The radio transceiver 81 is used for communication with an external device, in particular a programming device. Here, for example, measured values and/or parameters of the implant may be transmitted to the programming device. Changed parameters for the implant may also be received from the programming device.

The electronics module further comprises a control unit 83 (controller). The control unit 83 has a processor, for example a digital signal processor (DSP), a memory such as a RAM (random-access memory) and/or a ROM (read only memory), and a timer. As further functions, a memory access, for example DMA (direct memory access) and/or network functions such as MAC (media access control) may be integrated into the control unit 83.

A measuring unit 86 (sensing unit) is provided as a further component on the electronics module. The measuring unit 86 is configured to take measurements from the heart 91.

A pacemaker unit 85 (pacing unit) is configured to generate stimulation pulses for the heart 91.

The electronics module may optionally comprise a shocking unit 84 (shocking unit) and an HV unit 87 (HV—high voltage), especially if the implant is designed as an ICD. The shocking unit 84 is configured to control the HV unit 87. The HV unit 87 is configured to deliver a shock (defibrillation), for example with a voltage of 700-800 V.

An EMC (electromagnetic compatibility) unit 88 is provided and is designed to minimise or suppress the influence of electromagnetic fields. The electromagnetic fields may include spurious radiation, the field of a shock delivered by the HV unit 87, the field of a stimulation pulse delivered by the pacemaker unit 85, the field of an external shock, the field of an external stimulation, and fields from other external sources (for example a high-frequency measurement). The EMC unit 88 is coupled to the housing 92 of the implant.

The electronics module is coupled to a battery 90. A power unit 89 of the electronics module comprises a switched-mode power supply (SMPS) and is configured for power management.

The functions/units of the electronics module are implemented in various integrated circuits, i.e. chips mounted on the electronics module. The dimensions of the chips result from the complexity of their functions. The higher the complexity, the larger the planar dimensions of the chips. The size of the chips significantly determines the size of the electronics module and also its orientation in the implant (parallel to the energy store). The size of the electronics module is also determined by the number of electrical connections of the chips to one another, of the chips to the non-integrated passive components, and all other connections on the electronics module.

Which therapy functions may be monolithically integrated with each other on one chip by which production process or how many chips the electronics module contains depends on their working voltage range, their data and signal complexity, as well as on their character, i.e. whether they have an analogue, time-continuous or a digital, time-discrete or an analogue-digital, mixed signal behaviour. In principle, all the functions listed above may be monolithically integrated, in particular the digital control functions, the analogue-digital mixed sensing functions for ECG signal amplification and evaluation (ECG—electrocardiogram), the pacing for stimulation pulse generation, the power management for optimal power supply to the implant, and the shocking for voltage generation and control of the defibrillation shock. However, the currently used production processes with minimum structure sizes F=130 nm and F=180 nm result in chips whose dimensions are too large for a vertical arrangement in the implant housing and, moreover, whose data storage capacity (RAM) is too small or must be supplemented with another memory chip to enable all the required therapy and diagnosis functions. For the present implant, some or all of the functions of the electronics module are therefore implemented with chips manufactured with a minimum structure size $F\leq 90$ nm, preferably $F\leq 65$ nm or $F\leq 55$ nm.

One objective is to design the electronics module in such a way that it no longer determines the volume, shape and size of the implant (as in the prior art). To this end, at least one of the following rules is applied:

1. The electronics module is arranged parallel to the front side of the energy store.
2. The length of the electronics module is less than or equal to the length of the electrode connection device.
3. The width of the electronics module is less than or equal to the width of the energy store (or the width of the housing).
4. The length of the energy store is equal to the length of the electrode connection device (maximum volume utilisation).
5. The area of the electronics module corresponds to the area of the front side of the energy store.
6. The volume requirement of the electronics module is less than ¼ of the volume of the energy store (or less than ¼ of the total metal-enveloping volume of the implant).

Applying one or more of these rules results in a strip-shaped, narrow electronics module that is populated with components whose maximum edge length, including their connections, does not exceed the electronics module. Improved optical imaging and lithography processes in semiconductor production are enabling more and more functionality per silicon area. A minimum structure size of the components that is sufficient for production of the implant is $F\leq 90$ nm. This allows analogue, digital, analogue-digital mixed, and high-voltage circuits to be increasingly integrated monolithically on one chip. This reduces the number of chips and the number of connections on the electronics module, thus compensating for the smaller available area of the now narrow, strip-shaped module to enable the known functional complexity.

For the production of the integrated circuits on the electronics module, production processes with the following features are selected: At least one chip is produced in a process with a minimum structure size $F\leq 90$ nm. Alternatively, at least one chip is produced in a process with a minimum structure size $F\leq 65$ nm. Alternatively, at least one chip is produced in a process with minimum structure size $F\leq 65$ nm, to which a voltage of $\geq 10$ V with respect to its substrate may be connected simultaneously. Alternatively, at least one chip is produced in a process with a minimum structure size $F\leq 65$ nm, to which a voltage of $\geq 10$ V with respect to its substrate may be connected simultaneously and the SRAM (static random-access memory, static RAM) memory functions of the chip has a capacity of $\geq 3$ megabits.

The electronics module with the form factor described here is suitable for mounting in the cross-section of the flat implant, in particular between the energy store and the electrode connection device. This assembly location results in further features of the electronics module that may be realised individually or in any combination with each other:
- perpendicular connections for wired components on the top side and/or underside of the electronics module,
- bores, onto or through which connections of components, for example battery connections and/or header connections, may be plugged, and
- a bore fit to accommodate cutting sleeves and/or clamping sleeves.

Sawed, straight edges also enable optimal manufacture of the electronics module in panelised form in a standard packaging technique for Ball Grid Array Packages (µBGAs).

In a μBGA, the chips are assembled on a printed circuit board substrate (PCB substrate), bonded, and covered with a molding compound in a transfer overmolding process. Solder balls are applied to the back of the substrate for SMD assembly. The packaging takes place in the panelised state. The printed circuit board substrate always has a uniform panel size for all chip sizes, which only depends on the molding tool of the transfer molding machine. Depending on the chip size, more or fewer chips fit on the panel and are then sawn out of the panel in their final package size after potting and equipping with solder balls.

Figure 10A:
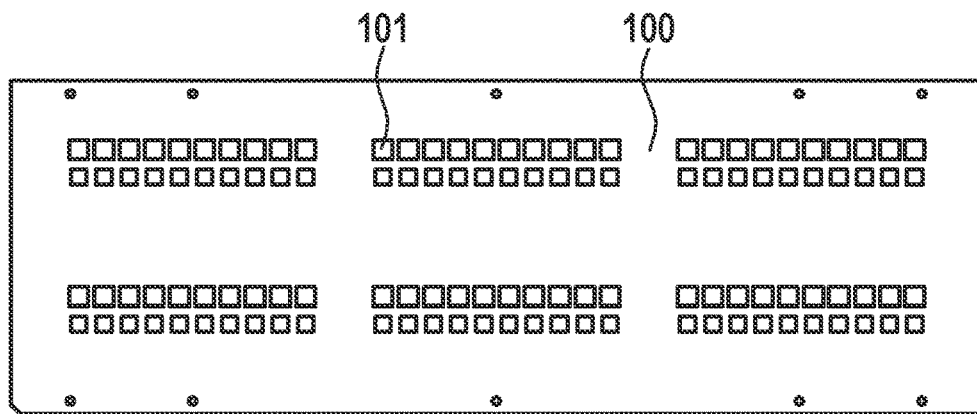
FIGS. 10A-10E show a production process for the electronics module.
Figure 10B:
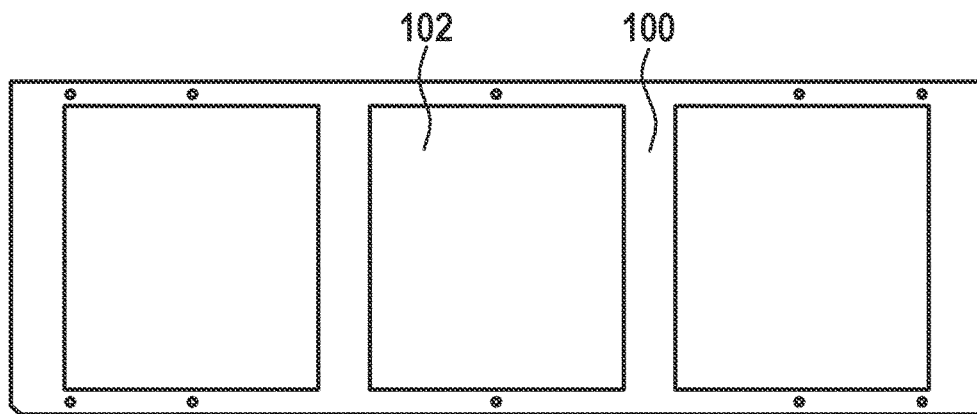

In one embodiment, there are three square potting areas, each with an edge length of 56 mm, on a 205 mm×70 mm panel, into which the chips are assembled and wire bonded (see FIGS. 10A and 10B). The application of this μBGA packaging process to the electronics module leads to further characteristics and extensions of the packaging process, which are shown in FIGS. 10A to 10E. After transfer molding, the holes or fits of the cutting sleeves and/or clamping sleeves are drilled (see FIG. 10C). The potting not only serves to cover the chips, it is also part of the mechanical stability of the electronics module and in particular of the resulting plug-in connection. Instead of solder balls, the panel is populated with the SMD components of the electronics modules in panelised form (see FIG. 10D). The edge lengths of the electronics module fulfil an integer divider ratio of the potting surface edges of the panel minus the sawing losses. The components of the electronics module may be provided as ASICs (application-specific integrated circuits).

Figure 10C:
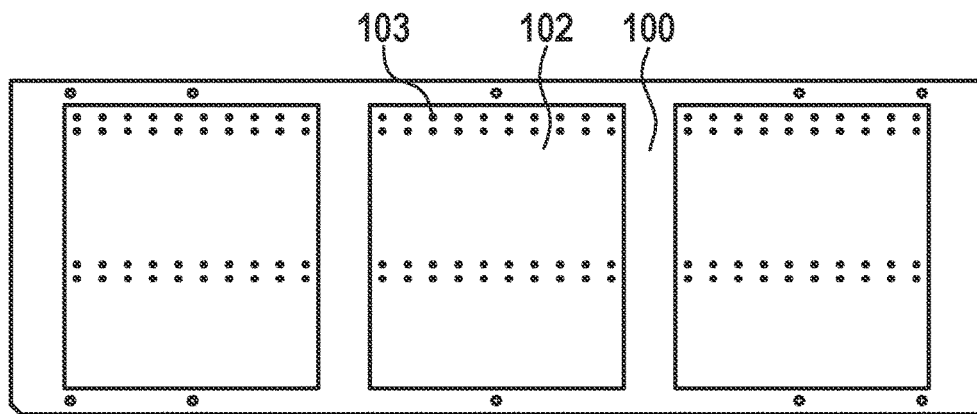
Figure 10D:
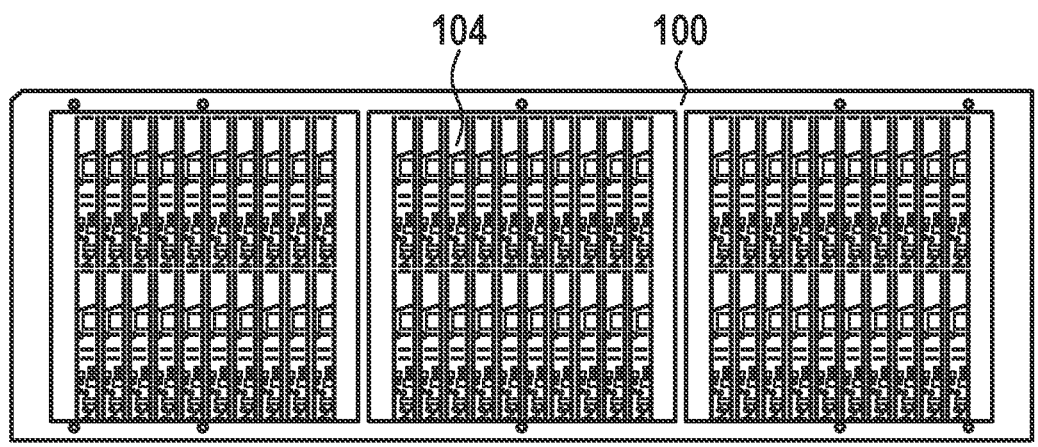
Figure 10E:
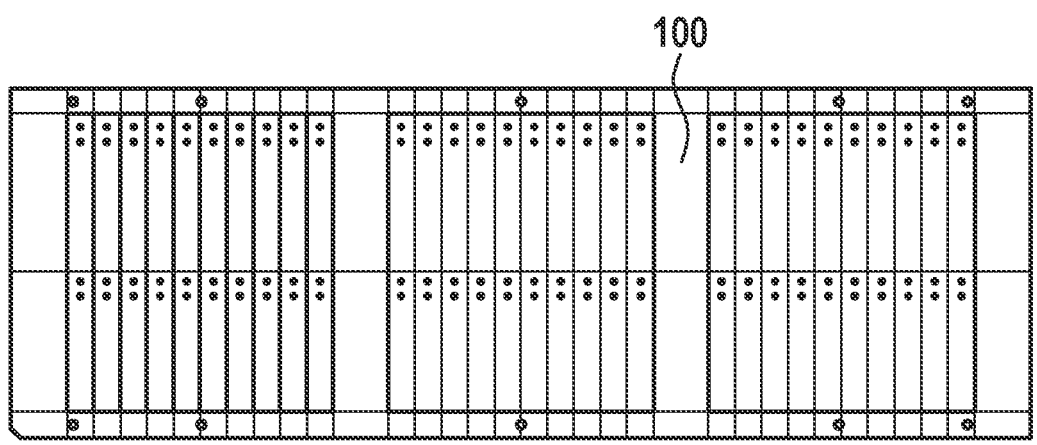

Some of the production steps are summarised below:
FIG. 10A: ASICs 101 in panelised form are assembled and bonded on a first side (front side) of the panel 100.
FIG. 10B: transfer overmolding of the assembled ASICs 101 with a potting agent 102.
FIG. 10C: drilling the holes 103 for a connection of the energy store.
FIG. 10D: population of a second side (rear side) of the panel 100 with SMD components 104.
FIG. 10E: sawing out the finished electronics modules.

FIGS. 11 to 17 show the individual steps for assembling an electrode connection device (header) on an implant. The steps are explained in more detail below.

Figure 11:
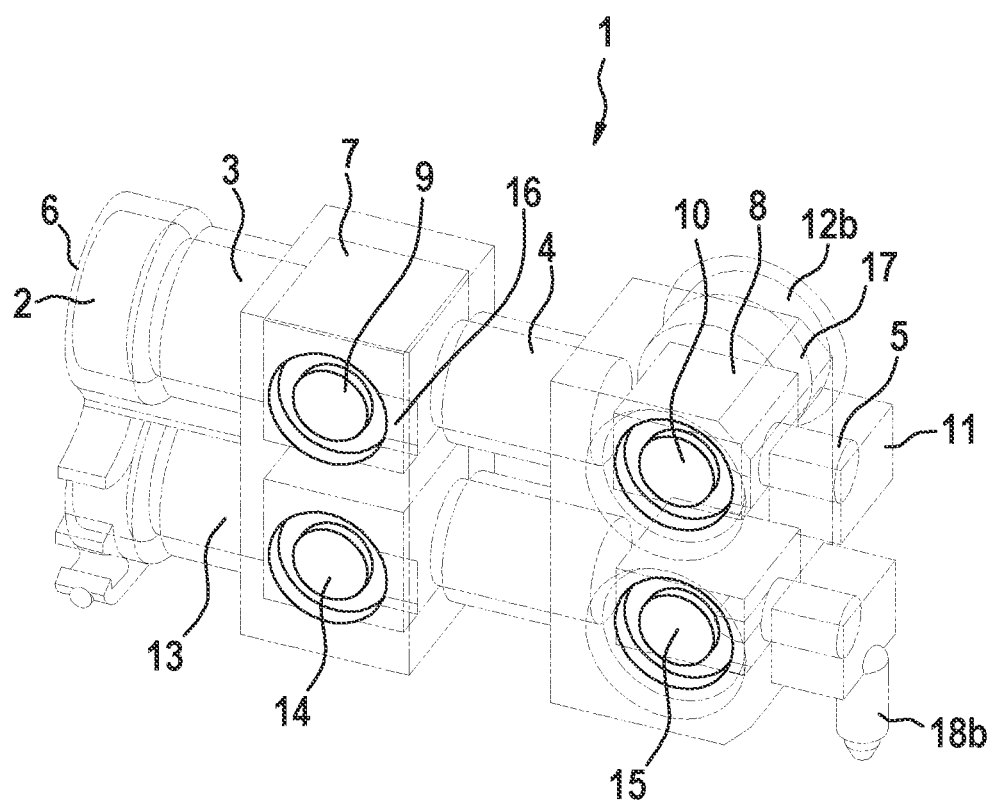
FIG. 11 shows a perspective view of an embodiment of an assembly for an electrode connection device.

FIG. 11 shows an assembly 1 (also referred to as a header core) with a first receiving means 2 for a male electrode connector and a second receiving means 13 for a further male electrode connector. The first receiving means 2 has a front opening 6, through which the male electrode connector may be inserted. The first receiving means 2 has a first portion 3, a second portion 4 and a third portion 5. The diameter of the first portion 3 is larger than the diameter of the second portion 4. The diameter of the second portion 4 is in turn larger than the diameter of the third portion 5. In other words, the first receiving means 2 is gradually tapered from the front opening 6 towards the end.

A first connection element is formed between the first portion 3 and the second portion 4 (i.e. in a front region of the first receiving means 2). A second connection element 8 is formed between the second portion 4 and the third portion 5 (in a rear region of the first receiving means 2). Both the first connection element 7 and the second connection element 8 have at least two flat side faces. This enables easy gripping of the assembly 1 during an assembly and enables automation of the assembly steps. In the embodiment shown, the first connection element 7 and the second connection element 8 are substantially cuboid-shaped. The second connection element 8 has a bevelled edge 17, which serves to save material and to observe the flow direction of the epoxy resin. A recess 12a is formed in the plastics material coating on a rear side of the first connection element 7. A rear opening 12b is formed on a rear side of the second connection element 8.

The assembly is partially surrounded by a plastics material 11. In the embodiment shown, the assembly is partially overmolded with polysulfone. Recesses for a first contact face 9 and a second contact face 10 are formed in the plastics material 11. The first and second contact faces are formed as circular faces. A guide 16 is formed adjacent to each of the first and second contact faces 9, 10. The guide 16 serves to receive a connection element (for example a wiring strip). The guides on the contact faces prevent connection elements from different contact faces from touching each other.

The second receiving means 13 is constructed analogously to the first receiving means 2. For reasons of clarity, the components of the second receiving means (an opening, the three step-shaped tapering portions and the two connection elements) are not provided with reference signs. The second receiving means also has two contact faces (third contact face 14 and fourth contact face 15) for connections. Guides are again formed adjacently to the contact faces.

A positioning means 18b is formed at one end of the second receiving means and is embodied as a pin with a pointed end. When assembling the assembly 1 on a housing 29 (see FIG. 15), the pointed end of the positioning means 18b may be inserted into a receptacle of the housing in order to facilitate the precisely fitting arrangement of the assembly on the housing. However, the assembly may also be embodied without positioning means 18b.

Figure 12:
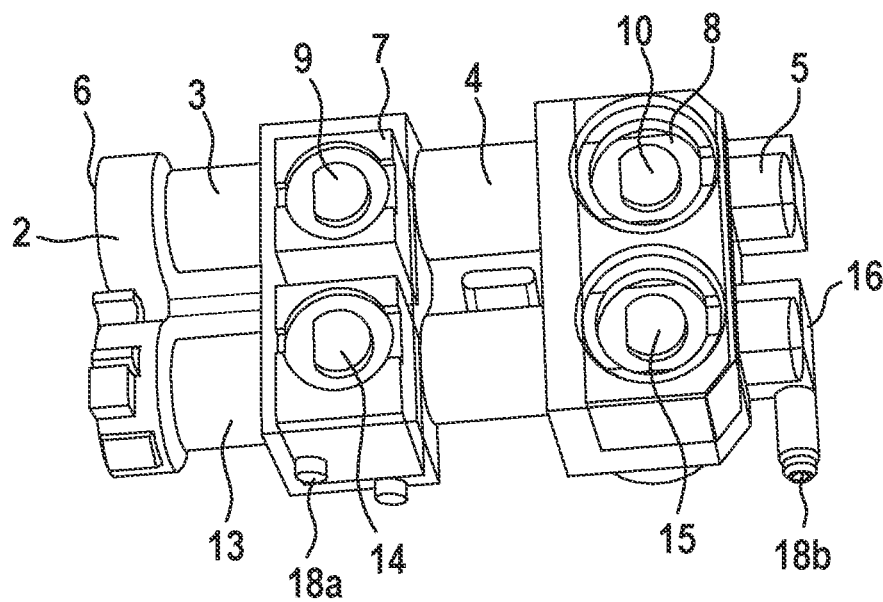
FIG. 12 shows a front view (upper image of FIG. 12) and a rear view (lower image of FIG. 12) of the assembly according to FIG. 11.
Figure 12:
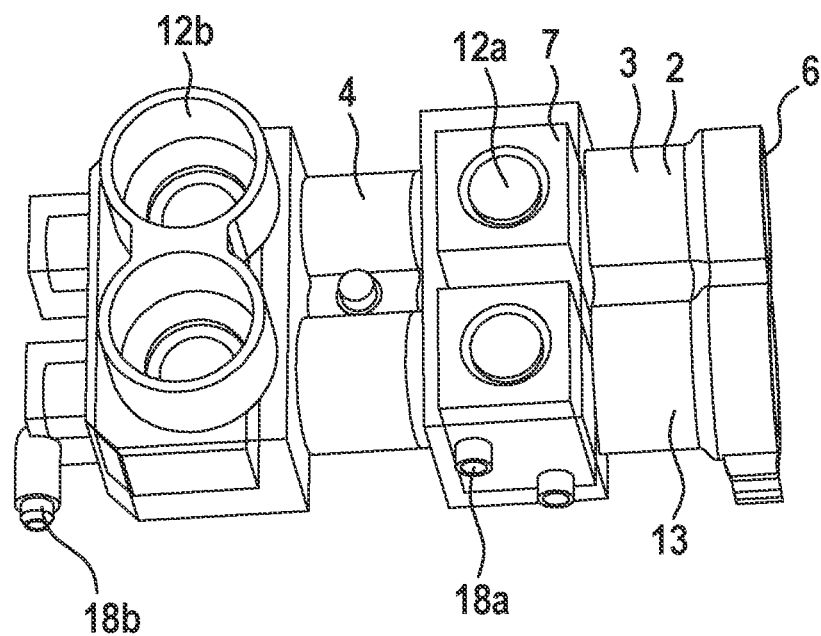

Positioning pins 18a are formed on an underside of the assembly (see FIG. 12). The positioning pins may be arranged in associated receptacles when the assembly is arranged on the housing of the implant. In the embodiment shown, two positioning pins are shown, but other numbers of positioning pins are possible.

The first receiving means 2 and the second receiving means 13 each have a spring sleeve and a male connector receptacle. The first receiving means 2 and the second receiving means 13 may be designed as IS-1 connectors.

Figure 13:
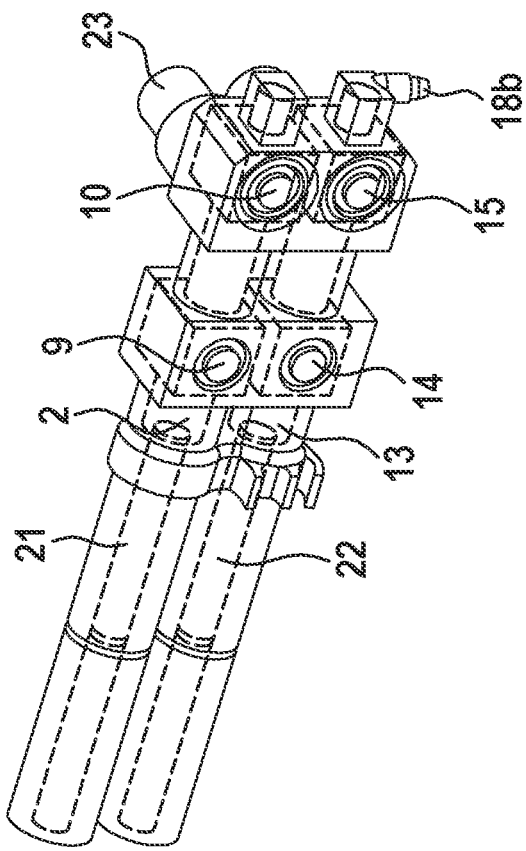
FIG. 13 shows the assembly according to FIGS. 11 and 12 with potting aids.
Figure 13:
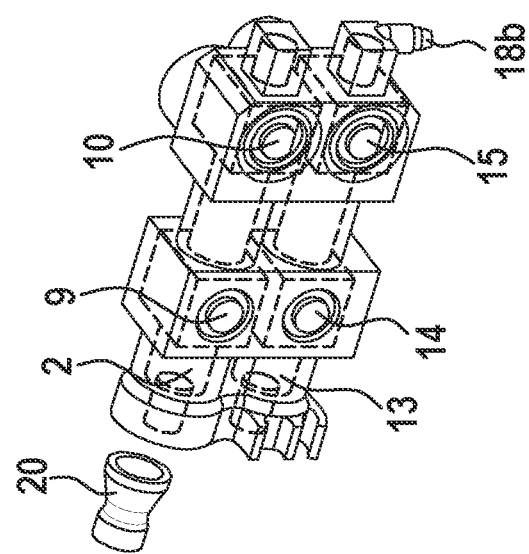

A spring element 20 is arranged in the first receiving means 2 and fastened there (left side of FIG. 13). The recess 12a in the plastics material is used to weld the spring element 20 arranged inside the first receiving means 2 into the first connection element 7 by means of resistance welding. Similarly, another spring element is arranged and fastened in the second receiving means 13 (not shown). The openings of the assembly 1 are then closed and sealed with potting aids 21, 22, 23 (right side of FIG. 13).

Figure 14:
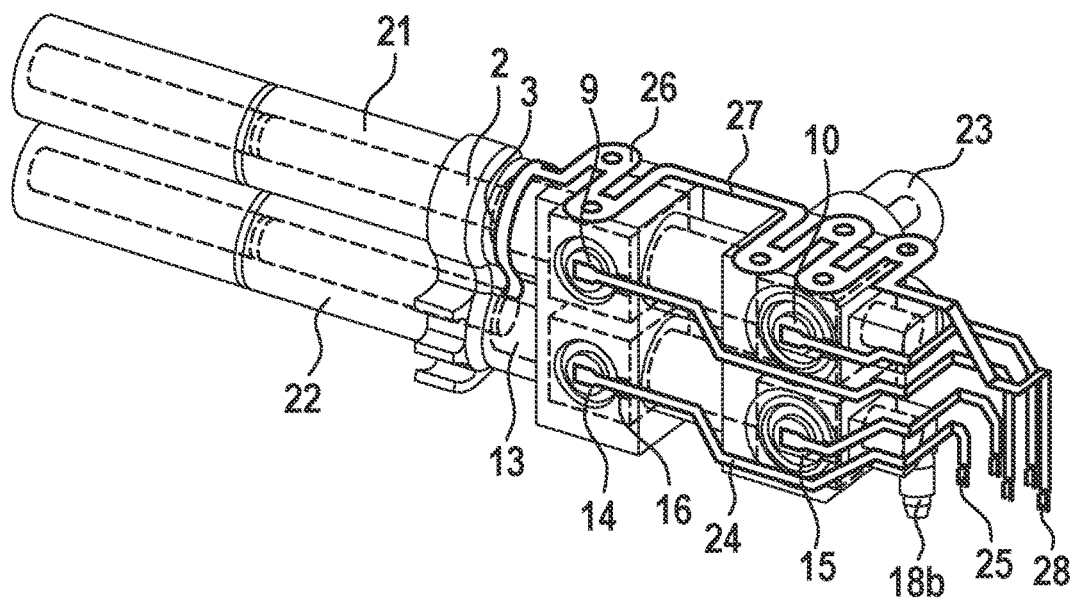
FIG. 14 shows the assembly according to FIGS. 11 to 13 with an antenna and conductors.
Figure 15:
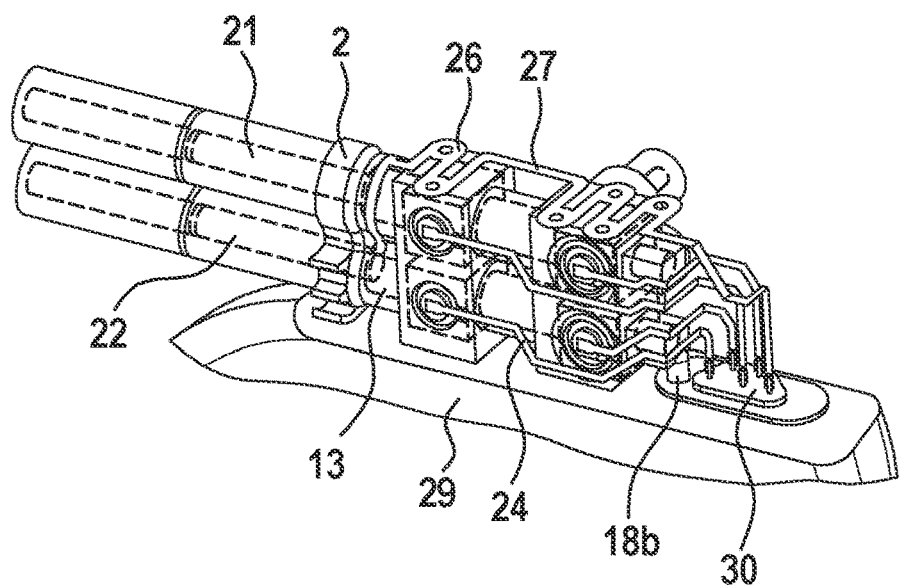
FIG. 15 shows the assembly according to FIGS. 11 to 14 arranged on a housing.
Figure 16:
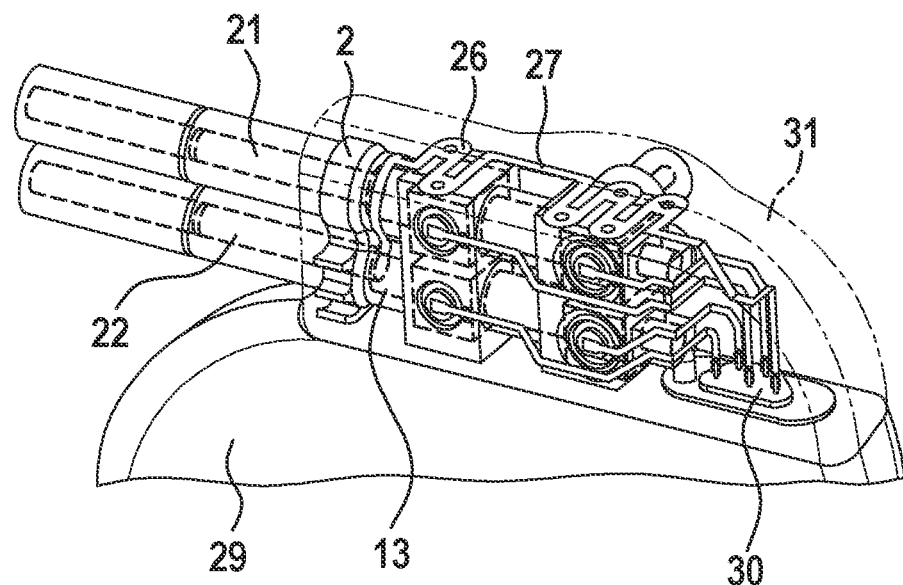
FIG. 16 shows the assembly according to FIGS. 11 to 15 completely potted (with potting aids)

A further assembly step is shown in FIG. 14. A wire strip 24 is fastened (for example welded) to the third contact face 14. At its rear end, the wire strip 24 has a wire strip connection 25, which is connectable to a pin contact of a feedthrough 30 (see FIG. 4) and may, for example, be plugged onto the pin contact. Further wire strips are connected to the other contact faces 9, 10, 15.

An antenna 26 is attached to the assembly 1. The antenna 26 partially surrounds the first portion 3 of the first receiving means 2 and is clipped thereto. In a region between the first connection element 7 and the second connection element 8, the antenna 26 has a U-shaped portion 27. This forms a grip recess that may be used, for example, with an automated gripper to hold and transport the assembly. An antenna connection 28 is formed at a rear end of the antenna for connection to the feedthrough 30.

The assembly with the wire strips and the antenna is then placed in a mold (for example a silicone mold) (not shown). The wire strip connections and the antenna connection 28 are placed on associated pins of the feedthrough 30 and are connected to the pins (for example welded). The mold is closed and filled with a synthetic resin 31 (for example epoxy resin). This forms the electrode connection device (see FIG. 16).

Figure 17:
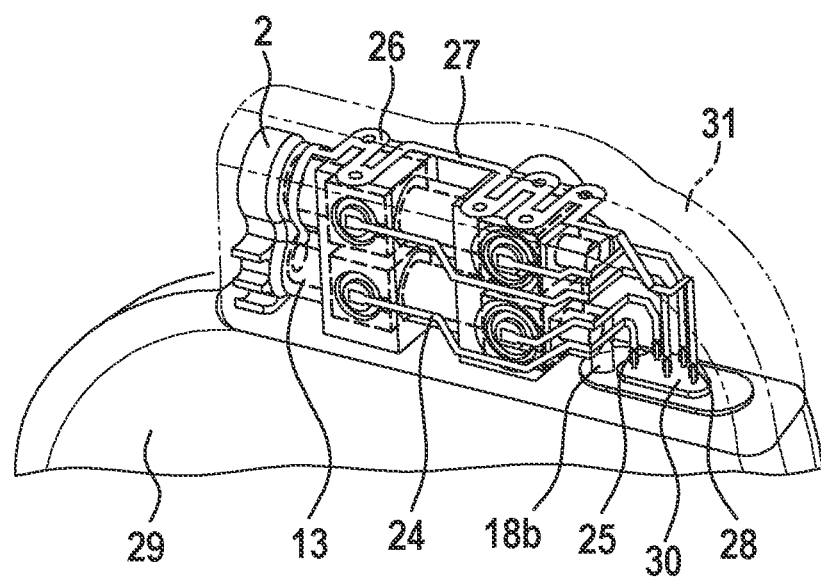
FIG. 17 shows the assembly according to FIGS. 11 to 15 completely potted (without potting aids)

The potting aids 21, 22, 23 are removed and any excess resin on the outer surfaces is removed, for example by grinding and/or polishing. The implant with the electrode connection device is now completely assembled (FIG. 17).

Figure 18:
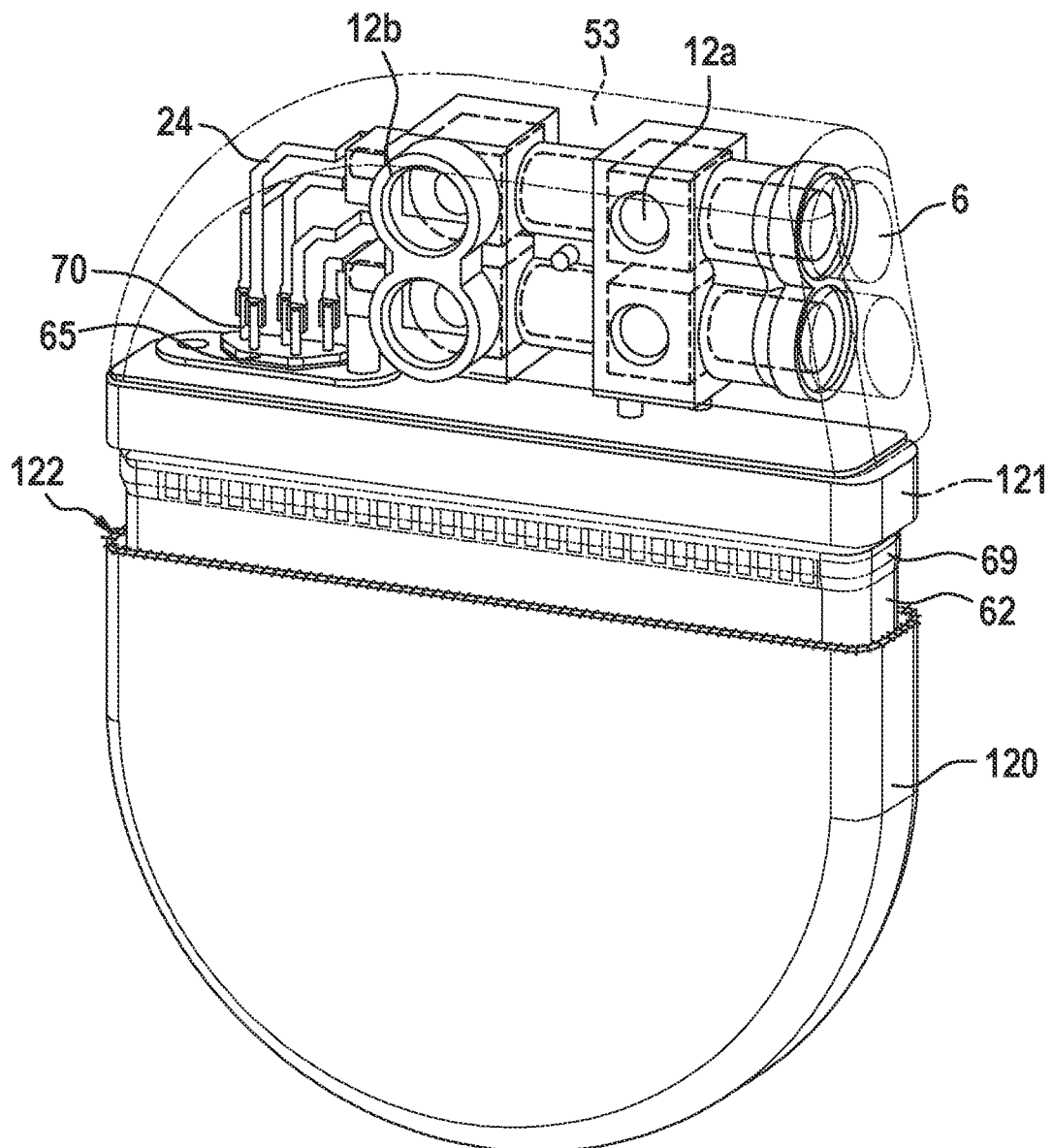
FIG. 18 shows another embodiment of an implant according to the present invention.

FIG. 18 shows another embodiment of the implant. The electrode connection device 53 is attached to a cover 121. The energy store 62 is received in a housing 120. The housing 120 may be provided as a deep-drawn molded part. The cover 121 is welded to the housing 120 along a circumferential weld seam 122 to close the housing 120. A support frame 69 is arranged on the energy store. The support frame 69 receives the electronics module. The electrode connection device 53 may be formed, for example, according to the embodiment shown in FIGS. 11 to 17. The feedthrough 65 with the pins 70 is welded into the cover 121.

The embodiments of the implant and methods disclosed herein may have the following advantages:

The internal structure of the electronic implant is significantly simplified, thus reducing production costs. Similarly, the number and complexity of the required production processes decreases, thus favouring the scalability of production (for example simplified transfer to other locations, reduced training needs for employees, reduced requirements for the required manufacturing environment and accompanying engineering). Furthermore, reworking becomes possible or simplified when detachable joining techniques are used.

With the form factor of the electronics module, the implant may be made smaller or the volume gained may be used to increase battery capacity and thus extend the service life of the implant. The production of the electronics module in μBGA technology enables an increase in the usefulness on the panel and an associated production cost saving. The vertical assembly of the electronics module (parallel to the front side of the energy store) enables electrical connections without angles and thus a simpler, more economical construction of the implant, optimised for automatic manufacturing in one axis.

The features disclosed in the description, the claims and the figures may be relevant for the realisation of embodiments both individually and in any combination with each other.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implant comprising:
   an electrode connection device;
   an electronics module; and
   an energy store,
   wherein
   the width of the electronics module is about equal to the width of the electrode connection device; the width of the electronics module and the width of the electrode connection device being measured in a direction corresponding to the smallest dimension of the implant; and
   the volume of the electronics module is less than 25% of the volume of the energy store.

2. The implant according to claim 1, wherein the ratio of the length of the electronic module to the width of the electronic module is 4:1 or more.

3. The implant according to claim 1, wherein the width of the electronic module is less than or equal to the width of the energy store.

4. The implant according to claim 1, wherein the length of the electronic module is less than or equal to the length of the energy store.

5. The implant according to claim 1, wherein the length of the electronic module is less than or equal to the length of the electrode connection device.

6. The implant according to claim 1, wherein the length of the energy store is less than or equal to the length of the electrode connection device, and/or wherein the width of the energy store is less than or equal to the width of the electrode connection device.

7. The implant according to claim 1, wherein the electronics module has a substrate, on which there are arranged a plurality of components, wherein the area of the substrate is smaller than or equal to the area of a front side of the energy store.

8. The implant according to claim 7, wherein some of the plurality of components have a minimum structure size of $F \leq 90$ nm.

9. The implant according to claim 7, wherein at least one of the plurality of components is arranged on a first side of the substrate, and wherein at least one other of the plurality of components is arranged on a second side of the substrate.

10. The implant according to claim 7, wherein some of the plurality of components are arranged as SMD (surface mounted device) elements on the substrate.

11. The implant according to claim 10, wherein some of the plurality of components are arranged in one or more Ball Grid Array (BGA) packages and/or Multi Chip Module (MCM) packages and/or as bare integrated circuits on the substrate.

12. The implant according to claim 7, wherein some of the plurality of components are arranged side by side or on top of each other on one side of the substrate, wherein the components are each connected to the substrate, and wherein the components are encapsulated with a potting agent.

13. The implant according to claim 12, wherein holes for a connection contact for the energy store and/or for a further connection contact for a feedthrough are formed in the potting agent.

14. The implant according to claim 1, wherein the electronics module is formed as a multi-chip module.

15. The implant according to claim 1, wherein a feedthrough to the electrode connection device is formed as a:
   integral component of the electronics module,
   SMD (surface mounted device) component on the electronics module, or
   plug-in connection on the electronics module.

* * * * *